(12) United States Patent
Wang et al.

(10) Patent No.: US 11,648,030 B2
(45) Date of Patent: May 16, 2023

(54) OSTOMY METHOD AND IMPLANTATION METHOD

(71) Applicant: Lifetech Scientific (Shenzhen) Co., Ltd., Shenzhen (CN)

(72) Inventors: Xiaodong Wang, Shenzhen (CN); Xianmiao Chen, Shenzhen (CN); Mingjuan Fu, Shenzhen (CN)

(73) Assignee: Lifetech Scientific (Shenzhen) Co, Ltd., Shenzhen (CN)

(*) Notice: Subject to any disclaimer, the term of this patent is extended or adjusted under 35 U.S.C. 154(b) by 360 days.

(21) Appl. No.: 17/102,150

(22) Filed: Nov. 23, 2020

(65) Prior Publication Data
US 2022/0160390 A1    May 26, 2022

(51) Int. Cl.
*A61B 17/34*    (2006.01)
*A61B 17/00*    (2006.01)

(52) U.S. Cl.
CPC .... *A61B 17/3403* (2013.01); *A61B 17/00234* (2013.01); *A61B 2017/00044* (2013.01); *A61B 2017/00247* (2013.01); *A61B 2017/3413* (2013.01)

(58) Field of Classification Search
CPC .......... A61B 17/00234; A61B 17/0057; A61B 17/3403; A61B 17/3468; A61B 17/3478; A61B 2017/00044; A61B 2017/00247; A61B 2017/00252; A61B 2017/00358; A61B 2017/00575; A61B 2017/00606; A61B 2017/22038; A61B 2017/3413
See application file for complete search history.

(56) References Cited

U.S. PATENT DOCUMENTS

2007/0049971 A1 * 3/2007 Chin .................. A61M 25/1011
606/232

* cited by examiner

*Primary Examiner* — Mohamed G Gabr
(74) *Attorney, Agent, or Firm* — Raymond Sun

(57) ABSTRACT

The present disclosure relates to an ostomy method and an implantation method. The ostomy method includes steps of making an incision in the chest to expose the heart, puncturing the left ventricle with a puncture needle, thrusting the puncture needle into the ventricular septum and then into the right ventricle to form a puncture site on the ventricular septum, and dilating the puncture site of the ventricular septum with a dilator to form an opening. The method of the present disclosure can reduce the death rate.

20 Claims, 8 Drawing Sheets

OSTOMY METHOD AND IMPLANTATION METHOD

TECHNICAL FIELD

The present disclosure relates to the field of medical devices, in particular to an ostomy method and an implantation method.

BACKGROUND ART

This section provides background information related to the present disclosure only and is not necessarily the prior art.

Congenital heart diseases have a certain incidence in neonates. A ventricular septal defect is a type of congenital heart disease with the highest incidence rate, and most likely to cause severe pulmonary hypertension. Implantation of an occluder to treat the congenital heart diseases is a currently widely used therapy.

In the research and development of any particular occluder, before it can be implanted into a human body for clinical trials, the safety and the feasibility need to be verified through animal tests. For implanting an occluder into the heart of an animal, the current common method is to implant the occluder through the stoma of the septal tissue of the animal heart. A widely used ostomy method is to dissect the sternum layer by layer from the median sternal line, saw the sternum along the midline with a wire saw, open the pericardium and free the great vessels. A puncture outfit is introduced into the right atrium via the open right atrial appendage. After the heart is fixed, the puncture outfit is rapidly thrust into the left ventricle in a direction perpendicular to the ventricular septum, forcibly thrust through the ventricular septum to finally dilate a puncture site.

This puncture method mainly has a few shortcomings: First, the animal operating procedures are complex, and it is easy to cause the animal's heart rate arrhythmia and possibly death during the implementation process. Second, during the puncture process, the puncture outfit easily tears the right atrium during the process of entering and exiting the right atrium, and also easily damages the surrounding great vessels to possibly cause massive hemorrhage which is difficult to repair, so that the animal would die. Third, the injury to the animal during the entire test is relatively large because the sternum needs to be sawn and the right atrial appendage needs to be removed, resulting in a relatively high death rate for the animal.

SUMMARY OF THE DISCLOSURE

In view of this, it is necessary to provide an ostomy method that reduces the death rate.

Further provided is an implantation method that reduces the death rate.

An ostomy method includes the steps of:
making an incision in the chest to expose the heart;
puncturing the left ventricle wall with a puncture needle;
thrusting the puncture needle into the ventricular septum and then into the right ventricle to form a puncture site on the ventricular septum; and
dilating the puncture site of the ventricular septum with a dilator to form an opening.

In one of the embodiments, the step of puncturing the left ventricle with a puncture needle and the step of thrusting the puncture needle into the ventricular septum wall and then into the right ventricle to form a puncture site on the ventricular septum are carried out under ultrasound guidance, and the puncture needle is perpendicular or substantially perpendicular to the ventricular septum when the puncture needle is thrust into the ventricular septum.

In one of the embodiments, before the step of dilating the puncture site of the ventricular septum with a dilator, the ostomy method further includes threading a guide wire into the puncture needle, and establishing a path communicating the femoral vein, the inferior vena cava, the superior vena cava, the right atrium, the right ventricle and the left ventricle after the guide wire is captured by a capturer.

In one of the embodiments, the guide wire has two free ends located outside a living body, wherein one free end is close to the femoral vein and the other one is close to the left ventricle.

In one of the embodiments, the step of dilating the puncture site of the ventricular septum with a dilator includes introducing the dilator from the free end, close to the left ventricle, of the guide wire along the guide wire into the ventricular septum via the left ventricle to dilate the puncture site to form the opening.

In one of the embodiments, the step of dilating the puncture site of the ventricular septum with a dilator includes introducing the dilator from the free end, close to the femoral vein, of the guide wire along the guide wire into the ventricular septum via a path communicating the femoral vein, inferior vena cava, superior vena cava, right atrium and right ventricle to dilate the puncture site to form the opening.

In one of the embodiments, the step of establishing a path communicating the femoral vein, the inferior vena cava, the superior vena cava, the right atrium, the right ventricle and the left ventricle after the guide wire is captured by a capturer includes:
introducing the capturer from a path communicating the femoral vein, the inferior vena cava, the superior vena cava, the right atrium, and the right ventricle, or from a path communicating the femoral vein, the inferior vena cava, and the superior vena cava; and
withdrawing the capturer along a path communicating the right ventricle, the right atrium, the superior vena cava, the inferior vena cava, and the femoral vein, or along a path communicating the superior vena cava, the inferior vena cava, and the femoral vein releasing the guide wire, thereby establishing a path communicating the femoral vein, the inferior vena cava, the superior vena cava, the right atrium, the right ventricle and the left ventricle.

In one of the embodiments, the ostomy method is performed under electrocardiographic monitoring.

An ostomy method according to another embodiment includes the steps of:
making an incision in the chest to expose the heart;
puncturing the left ventricle wall with a puncture needle;
thrusting the puncture needle into the ventricular septum and then into the right ventricle to form a puncture site on the ventricular septum;
threading a guide wire into the puncture needle to introduce the guide wire into a living body; and
introducing a dilator along the guide wire into the ventricular septum to dilate the puncture site to form an opening.

In one of the embodiments, in the step of introducing a dilator along the guide wire into the ventricular septum to dilate the puncture site to form an opening, the dilator is introduced along the guide wire from the left ventricle into the ventricular septum.

In one of the embodiments, before the step of introducing a dilator along the guide wire into the ventricular septum to dilate the puncture site to form an opening, the ostomy method further includes establishing a path communicating the femoral vein, the inferior vena cava, the superior vena cava, the right atrium, the right ventricle and the left ventricle after the guide wire is captured by a capturer; and in the step of introducing a dilator along the guide wire into the ventricular septum to dilate the puncture site to form an opening, the dilator is introduced into the ventricular septum along the guide wire from a path communicating the femoral vein, the inferior vena cava, the superior vena cava, the right atrium, and the right ventricle.

In one of the embodiments, the step of puncturing the left ventricle with a puncture needle and the step of thrusting the puncture needle into the ventricular septum and then into the right ventricle to form a puncture site on the ventricular septum are carried out under ultrasound guidance, and the puncture needle is perpendicular or substantially perpendicular to the ventricular septum when the puncture needle is thrust into the ventricular septum.

Yet another embodiment of an implantation method includes the steps of:

making an incision in the chest to expose the heart;
puncturing the left ventricle with a puncture needle;
thrusting the puncture needle into the ventricular septum and then into the right ventricle to form a puncture site on the ventricular septum;
dilating the puncture site of the ventricular septum with a dilator to form an opening; and
delivering an occluder to the opening site and releasing the occluder to occlude the opening.

In one of the embodiments, before the step of dilating the puncture site of the ventricular septum with a dilator, the implantation method further includes threading a guide wire into the puncture needle, and establishing a path communicating the femoral vein, the inferior vena cava, the superior vena cava, the right atrium, the right ventricle and the left ventricle after the guide wire is captured by a capturer.

In one of the embodiments, the step of dilating the puncture site of the ventricular septum with a dilator to form an opening includes introducing the dilator along the guide wire from the left ventricle into the ventricular septum to dilate the puncture site to form the opening.

In one of the embodiments, before the step of delivering an occluder to the opening site and releasing the occluder to occlude the opening, the implantation method further includes a step of withdrawing the dilator out of a living body from the left ventricle.

In one of the embodiments, in the step of delivering an occluder to the opening site and releasing the occluder to occlude the opening, the occlude is delivered along a delivery path that communicates the femoral vein, the inferior vena cava, the superior vena cava, the right atrium, and the right ventricle-ventricular septum.

In one of the embodiments, the step of dilating the puncture site of the ventricular septum with a dilator to form an opening includes introducing the dilator along the guide wire into the ventricular septum from a path communicating the femoral vein, the inferior vena cava, the superior vena cava, the right atrium, the right ventricle, and the ventricular septum to dilate the puncture site to form the opening.

In one of the embodiments, before the step of delivering an occluder to the opening site and releasing the occluder to occlude the opening, the implantation method further includes withdrawing the dilator out of a living body from the ventricular septum, the right ventricle, the right atrium, the superior vena cava, the inferior vena cava and the femoral vein.

In one of the embodiments, the step of puncturing the left ventricle with a puncture needle and the step of thrusting the puncture needle into the ventricular septum and then into the right ventricle to form a puncture site on the ventricular septum are carried out under ultrasound guidance, and the puncture needle is perpendicular or substantially perpendicular to the ventricular septum when the puncture needle is thrust into the ventricular septum.

The above-described ostomy method requires no thoracotomy, and after the ventricular septum is punctured directly from the left ventricle, the puncture site is dilated with the dilator to form the opening. Compared with the existing method, the method of the present disclosure can avoid the damage caused by thoracotomy; and furthermore, does not damage the surrounding great vessels, and the right atrial appendage does not need to removed, which can reduce the death rate.

In the implantation method of the present disclosure, the ostomy method reduces the death rate, and improves the implantation success rate.

DETAILED DESCRIPTION OF THE DISCLOSURE

To make the above objectives, features and advantages of the present disclosure more outstanding and understandable, the specific implementation modes of the present disclosure are described below in detail in conjunction with the accompanying drawings. In the following description, numerous specific details are set forth in order to provide a thorough understanding of the present disclosure. However, the present disclosure can be embodied in many different forms than those herein set forth, and such modifications as would occur to those skilled in the art may be made without departing from the spirit and scope of the present disclosure. Therefore, the present disclosure is not limited to the specific implementation disclosed below.

Unless defined otherwise, all technical and scientific terms used herein have the same meaning as commonly understood by those skilled in the art to which the present disclosure belongs. The terms used in the description of the present disclosure herein is for the purpose of describing particular embodiments only and is not intended to limit the present disclosure.

Figure 1:
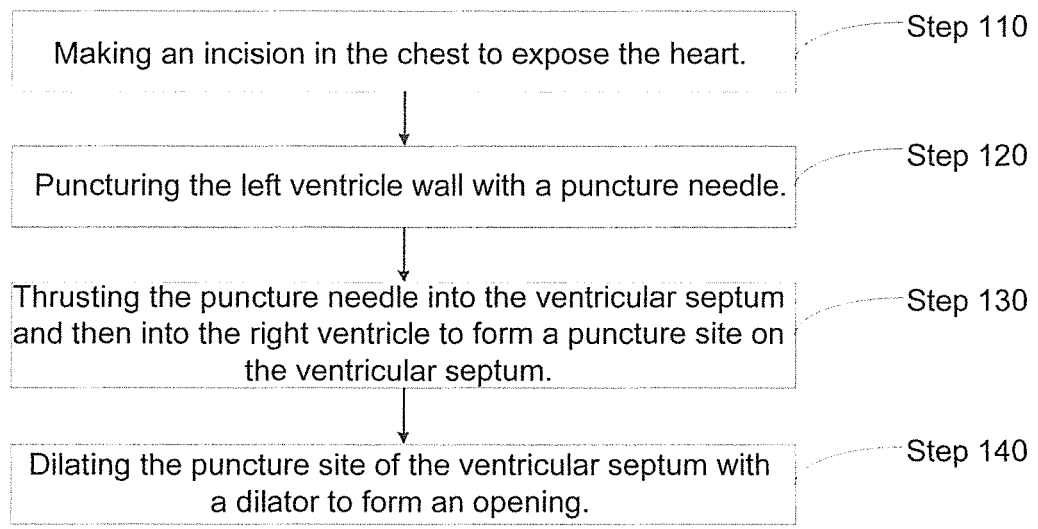
FIG. 1 is a flow chart of an ostomy method according to one embodiment of the present disclosure.

Referring to FIG. 1, an ostomy method according to one embodiment of the present disclosure includes the following steps:

Step 110: Making an incision in the chest to expose the heart.

Figure 2:
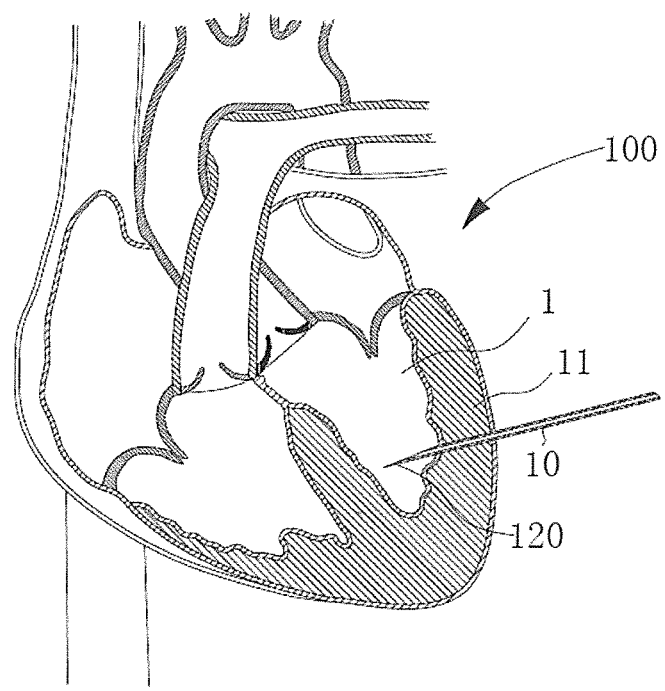
FIG. 2 is a schematic diagram showing the puncturing of the left ventricle with a puncture needle of an ostomy method according to one embodiment of the present disclosure.

Under electrocardiographic monitoring, an incision is made in the chest of a subject (e.g. a human or an animal, the animal being a pig or dog, etc.), and is dilated with a spreader to expose the heart 100, as shown in FIG. 2. After the heart 100 is exposed, the pericardium is cut and suspended, and the heart wall is exposed.

The subject needs to fast for 6 hours before the operation, and is subjected to ostomy under electrocardiogram monitoring after being anesthetized. An animal serving as a subject is taken for example. In the surgical procedure, the animal lies down on the right side, and is fixed, and an opening is made in the left inner shoulder part (the bone-free part) of the animal.

In one embodiment, the left internal shoulder part is a left position between a fourth rib and a fifth rib.

Step 120: Puncturing the left ventricle wall with a puncture needle.

Figure 3:
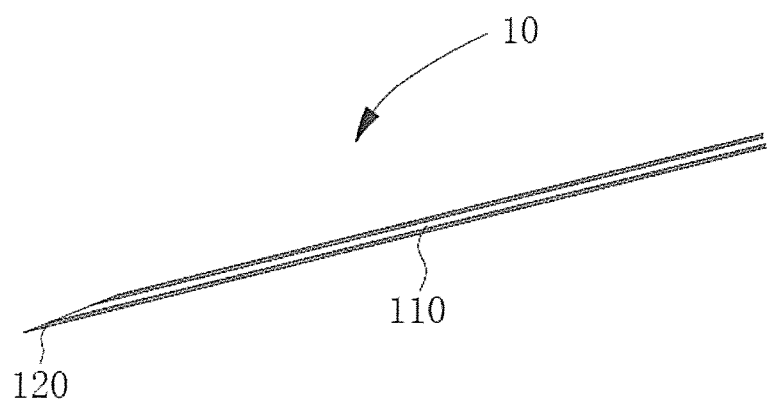
FIG. 3 is a schematic structural diagram of a puncture needle according to one embodiment of the present disclosure.

Referring to FIG. 3, the puncture needle 10 is of a thin strip-like structure having a through hole 110 formed inside and extending axially from one end to the other end, and one end is provided with a tip 120 convenient for puncturing.

Returning to FIG. 2, the puncture needle 10 is thrust into the left ventricle 1 from the left ventricle wall 11, and the tip 120 of the puncture needle 10 is introduced into the left ventricle 1. The puncture process is carried out under ultrasound guidance, to avoid excessive puncture that would damage the right ventricular wall, so that the operation accuracy can be improved.

Step 130: Thrusting the puncture needle into the ventricular septum and then into the right ventricle to form a puncture site on the ventricular septum.

Figure 4:
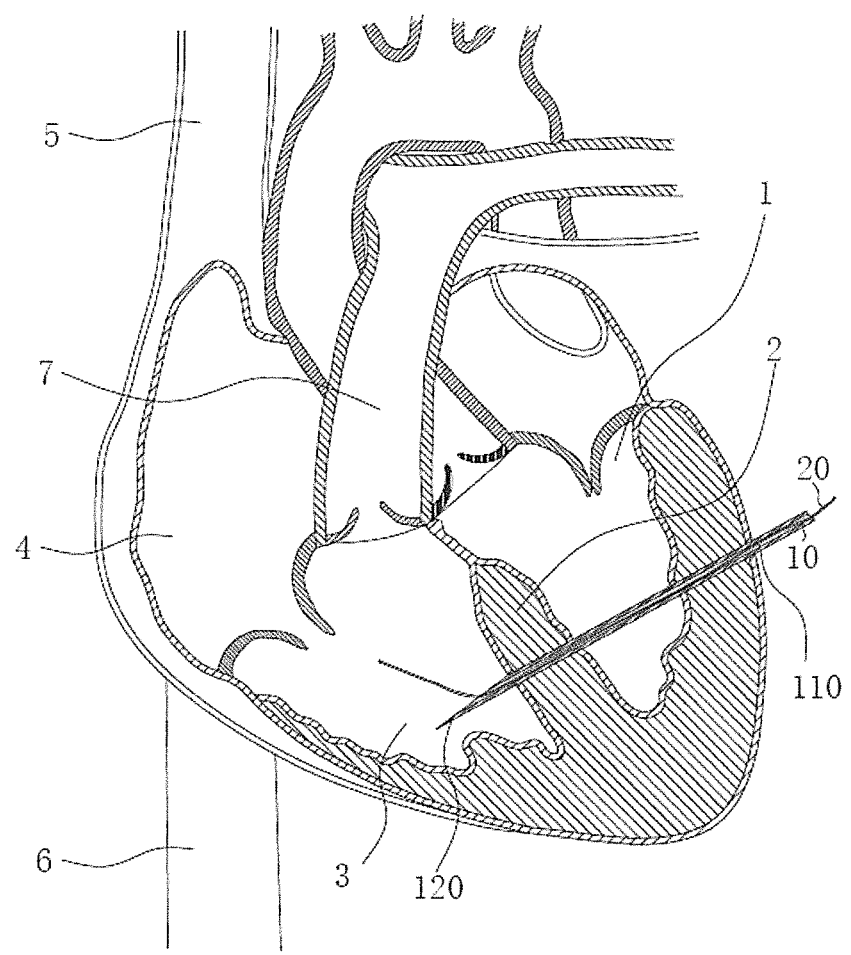
FIG. 4 is a schematic structural diagram showing the threading of a guide wire into a puncture needle to introduce the guide wire into a living body from the left ventricle via the ventricular septum of an ostomy method according to one embodiment of the present disclosure.

Referring to FIG. 4, under ultrasound guidance, after the position of the puncture needle 10 is adjusted, the puncture needle 10 is inserted into the interventricular septum 2, and the tip 120 is introduced into the right ventricle 3, so that a puncture site on the ventricular septum 2 is formed.

When the puncture needle 10 is inserted into the interventricular septum 2, the puncture needle 10 is perpendicular or substantially perpendicular to the ventricular septum 2. The substantially perpendicular state means that the puncture needle 10 is at an angle of 90 degrees±15 degrees to the ventricular septum 2.

Step 140: Dilating the puncture site of the ventricular septum with a dilator to form an opening.

In one embodiment, the dilator is a balloon.

With continued reference to FIG. 4, a guide wire 20 is threaded into the through hole 110 of the puncture needle 10 from the outside of the heart and is introduced into the right ventricle 3 along the through hole 110. Next, the puncture needle 10 is withdrawn to the outside of the heart. Next, a balloon (not shown) is delivered into the ventricular septum 2 along the guide wire 20, and the balloon is dilated by using a method known to those skilled in the art to dilate the puncture site to form the opening. For example, fluid, such as water and saline, may be injected into the balloon to dilate the balloon. According to the method, the balloon is delivered into the puncture site of the ventricular septum 2, so that the delivery path is short, and the delivery is convenient; and furthermore, the balloon can be conveniently dilated, which is favorable for reducing the operation time.

In another embodiment, the balloon is delivered into the puncture site of the ventricular septum 2 from a path that includes the femoral vein (not shown), inferior vena cava 6, superior vena cava 5, right atrium 4, right ventricle 3, and ventricular septum 2 by using a method known to those skilled in the art. For example, the guide wire 20 is introduced into the through hole 110 of the puncture needle 10 according to the path of the femoral vein, inferior vena cava 6, superior vena cava 5, right atrium 4, right ventricle 3.

This ostomy method requires no thoracotomy, and after the ventricular septum 2 is punctured directly from the left ventricle 1, the puncture site is dilated with the balloon to form the opening. Compared with existing methods, this method of the present disclosure can avoid the damage caused by thoracotomy; furthermore, this method does not damage the surrounding great vessels, and the right atrial appendage does not need to be removed, which can reduce the death rate.

It should be noted that the puncture site of the ventricular septum 2 is dilated with the balloon, and the operations of injecting the fluid to dilate the balloon and discharging the fluid are repeated for multiple times to slowly make the incision, thereby avoiding excessive injury to the ventricular septum 2.

Figure 5:
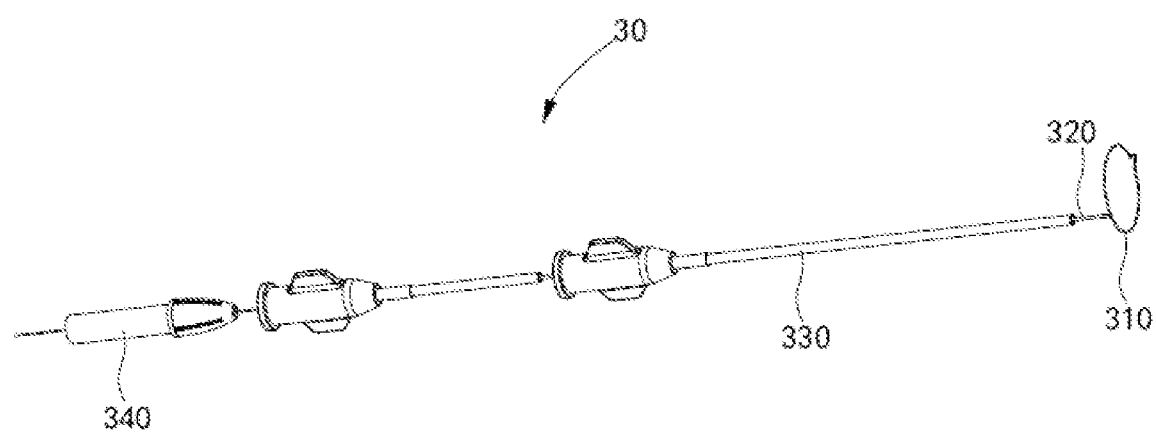
FIG. 5 is a schematic structural diagram of a capturer according to one embodiment of the present disclosure.
Figure 6:
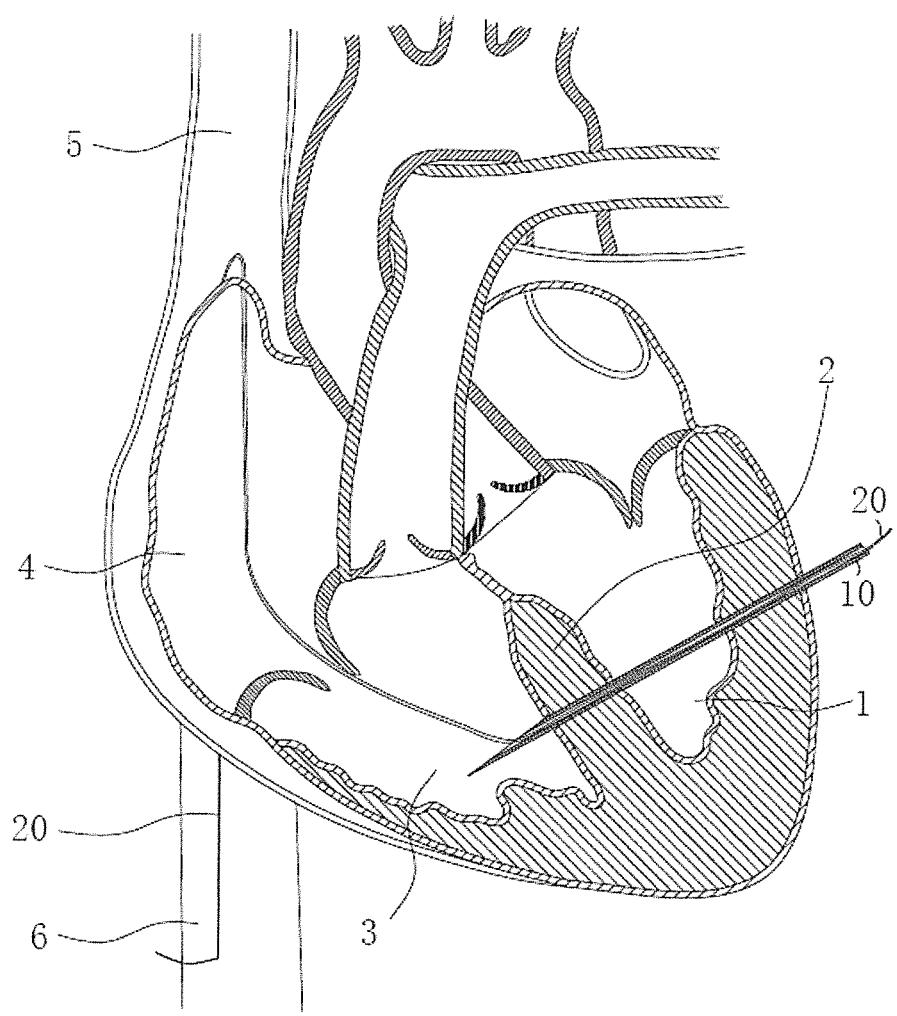
FIG. 6 is a schematic diagram showing the capturing of a guide wire according to one embodiment of the present disclosure.

In one embodiment, before the step that the puncture site of the ventricular septum 2 is dilated with the balloon, after the guide wire 20 is threaded into the puncture needle 10, the method further includes establishing a path communicating the femoral vein, the inferior vena cava 6, the superior vena cava 5, the right atrium 4, the right ventricle 3, and the left ventricle 1 after using a capturer 30 (as shown in FIG. 5) to capture the guide wire 20. As shown in FIG. 6, the guide wire 20 is extended from the left ventricle 1 via the ventricular septum 2 to the right ventricle 3, the right atrium 4, the superior vena cava 5, the inferior vena cava 6, and the femoral vein (not shown) in sequence. The guide wire 20 has two free ends, wherein one free end is close to the left ventricle 1, and the other one is close to the femoral vein.

Referring back to FIG. 5, the capturer 30 includes a capturing ring 310, a connecting rod 320, a capturing catheter 330 and an operation handle 340. The proximal ends of the connecting rod 320 and the capturing catheter 330 are connected to the operation handle 340; the distal end of the connecting rod 320 is connected to the capturing ring 310; and the connecting rod 320 is movably accommodated inside the capturing catheter 330. By operating the operation handle 340, the connecting rod 320 is slid axially along the capturing catheter 330 so that the capturing ring 310 slides from the capturing catheter 330 to the outside, or enters the capturing catheter 330 from the outside. Furthermore, after the guide wire 20 is captured by the capturing ring 310, the capturing ring 310 can be controlled, by the operation handle 340, to turn from a naturally expanding state (the state as shown in FIG. 5) into a tightened state to tightly clamp the guide wire 20. After the guide wire 20 is tightly clamped by the capturing ring 310, the connecting rod 320 and the capture ring 310 are accommodated in the capturing catheter 330 by the operation handle 340 to capture the guide wire 20.

Specifically, the capturer 30 is introduced into the vascular system from the femoral vein, and then into the right ventricle 3 sequentially via the inferior vena cava 6, the superior vena cava 5 and the right atrium 4. After the guide wire 20 is captured by the capturing ring 310 of the capturer 30, the capturing ring 310 is tightened, and the capturer 30 is withdrawn according to the path of right ventricle 3, right atrium 4, superior vena cava 5, inferior vena cava 6, and femoral vein, so as to bring the free end of the guide wire 20 away from the left atrium 1 out of the living body to a position near the femoral vein. Thus, the two free ends of the guide wire 20 will be located outside the living body. As shown in FIG. 6, one free end is located near the femoral vein, and the other free end is located near the left ventricle 1. The part between the two free ends is located in the living body.

Since both free ends of the guide wire 20 are located outside the living body and on the left and right sides, a left passageway (left ventricle 1, ventricular septum 2) and a right passageway (femoral vein, inferior vena cava 6, superior vena cava 5, right atrium 4, right ventricle 4, ventricular septum 2) are established.

In one embodiment, the balloon is introduced into the puncture site from the left passageway. The path of the left passageway is relatively short, so that the operation time is effectively shortened.

In another embodiment, the balloon is introduced into the puncture site from the right passageway.

The two passageways, namely the left passageway and the right passageway, are established through one guide wire 20, so that surgeons with different habits can conveniently select the passageways according to their operation habits, and the applicability is good. In addition, after the completion of the ostomy, when it is required to implant an interventional device (e.g. an occluder), the surgeon may also deliver the interventional device from either the left passageway or the right passageway according to their own personal operating habits.

In the embodiments described above, the guide wire 20 is captured by the capturer 30 in the right ventricle 3. In this embodiment, it is only necessary to penetrate the guide wire 20 through the ventricular septum 2, with one of the free ends of the guide wire 20 entering the right ventricle 3.

In one embodiment, after one free end of the guide wire 20 is introduced into the right ventricle 3, the guide wire 20 is continued to be pushed to enter the right atrium 4 or the superior vena cava 5, so that the guide wire 20 is captured by the capturer 30 in the right atrium 4 or the superior vena cava 5. Alternatively, after one free end of the guide wire 20 is introduced into the right ventricle 3, the guide wire 20 is continued to be pushed, so that the free end of the guide wire 20 is close to the pulmonary artery 7 (referring to FIG. 4), and the guide wire 20 is captured by the capturer 30 at a position close to the pulmonary artery 7. Since the guide wire 20 is captured at the right atrium 4, the superior vena cava 5 or the position close to the pulmonary artery 7, the influence of the chordae tendineae located in the right ventricle 4 can be avoided, the capturing step can be conveniently done, and damage to the chordae tendineae can be avoided.

In one embodiment, the step that establishes a path connecting the femoral vein, the inferior vena cava 6, the superior vena cava 5, the right atrium 4, the right ventricle 3, and the left ventricle 1 after using the capturer 30 to capture the guide wire 20 is carried out under radioactive imaging equipment, so that the capturer 30 and the guide wire 20 are conveniently observed, the operation is convenient, and the accuracy and safety of the operation are improved.

It should be noted that the dilator is not limited to balloons. In other embodiments, other dilators, such as a dilating sheath, may be used.

Figure 7:
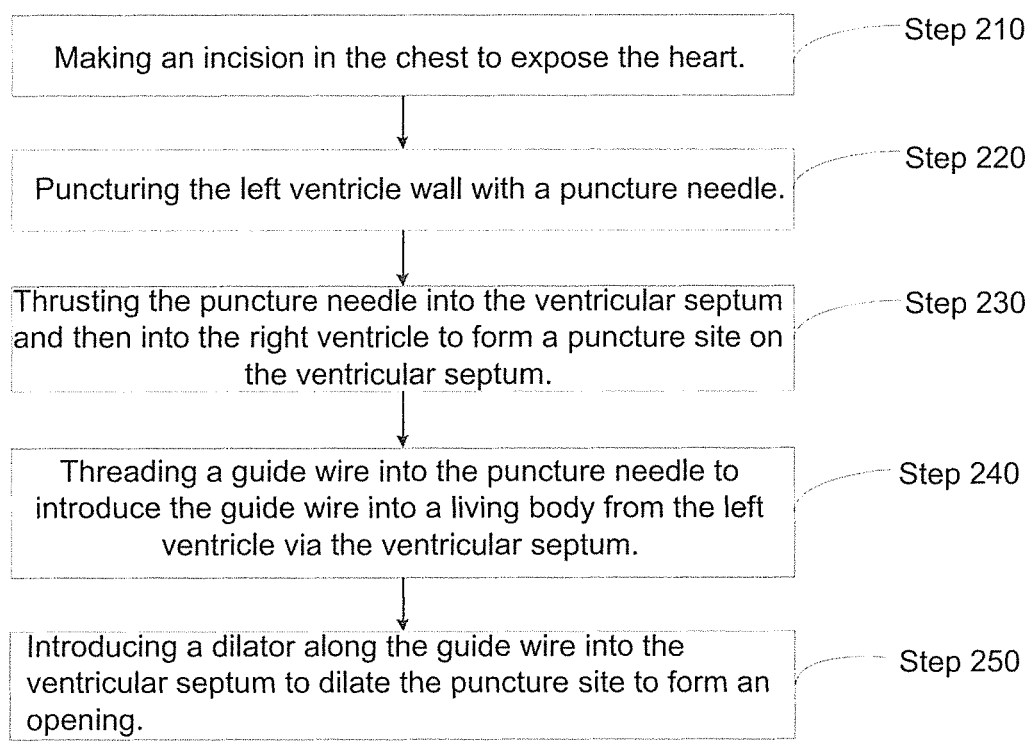
FIG. 7 is a flow chart of an ostomy method according to another embodiment of the present disclosure.

Referring to FIG. 7, an ostomy method of another embodiment includes the following steps:

Step 210: Making an incision in the chest to expose the heart.

Step 220: Puncturing the left ventricle wall with a puncture needle.

Step 230: Thrusting the puncture needle into the ventricular septum and then into the right ventricle to form a puncture site on the ventricular septum.

Steps 210, 220 and 230 are the same as steps 110, 120 and 130 respectively, and will not be described in detail herein.

Step 240: Threading a guide wire into the puncture needle to introduce the guide wire into a living body from the left ventricle via the ventricular septum.

Referring again to FIG. 4, the guide wire 20 is threaded from the outside of the heart into the through hole 110 of the puncture needle 10 and into the right ventricle 3 along the through hole 110. Next, the puncture needle 10 is withdrawn to the outside of the heart. In this state, one free end of the guide wire 20 is located in the right ventricle 3 or further is extended into the right atrium 4, and the other free end is located outside the living body and near the left ventricle 1, as shown in FIG. 4.

Step 250: Introducing a dilator along the guide wire into the ventricular septum to dilate the puncture site to form an opening.

The dilator may be a balloon, a dilating sheath, or a similar mechanism. The following is illustrated by a balloon.

The balloon is introduced into the left ventricle 1 from the free end, located near the left ventricle 1, of the guide wire 20 and further into the puncture site of the ventricular septum 2, and the puncture site is dilated by dilating the balloon to form the opening in the ventricular septum 2. The balloon is introduced into the ventricular septum 2 from the left ventricle 1 along the guide wire 20, so that the entering path is relatively short, the operation time is shortened as a whole, and the operation can be done conveniently.

In one embodiment, before the step that the puncture site of the ventricular septum 2 is dilated by using the balloon, after the guide wire 20 is threaded into the puncture needle 10, the method further includes the step of establishing a path communicating the femoral vein, the inferior vena cava 6, the superior vena cava 5, the right atrium 4, the right ventricle 3 and the left ventricle 1 after the guide wire 20 is captured by a capturer 30. The guide wire 20 is extended from the left ventricle 1 to the right ventricle 3, the right atrium 4, the superior vena cava 5, the inferior vena cava 6 and the femoral vein (not shown) in sequence, and is extended out of the living body from the femoral vein. The guide wire 20 has two free ends, wherein one free end is close to the left ventricle 1, and the other one is close to the femoral vein.

The other free end of the guide wire 20 is captured by the capturer 30 and then is sent out of the body. On one hand, the other end of the guide wire 20 can be fixed conveniently, and the operation for delivering the balloon through the left passageway is facilitated. On the other hand, since the two free ends of the guide wire 20 are located outside the living body and on the left and the right sides, a left passageway and a right passageway are established, so that an interventional device can be implanted favorably through the right passageway.

In another embodiment, the step that a free end of the guide wire 20 is pulled out of the body by the capturer 30 is omitted, so that Step 250 is directly implemented. For example, the balloon is delivered and dilated through the left passageway. Furthermore, after Step 250 is completed, i.e. after the completion of the ostomy, before the interventional device is implanted, the method further includes establishing a path communicating the femoral vein, the inferior vena cava 6, the superior vena cava 5, the right atrium 4, the right ventricle 3 and the left ventricle 1 after the guide wire 20 is captured by a capturer 30. The guide wire 20 is extended from the left ventricle 1 via the ventricular septum 2 to the right ventricle 3, the right atrium 4, the superior vena cava 5, the inferior vena cava 6 and the femoral vein (not shown) in sequence, and is extended out of the living body from the femoral vein to establish a right passageway through which the interventional device can be subsequently implanted.

The above ostomy method requires no thoracotomy, and after the ventricular septum 2 is punctured directly from the left ventricle 1, the puncture site is dilated with the balloon or other dilators to form the opening. Compared with the existing method, the method of the present disclosure can avoid the damage caused by a thoracotomy; and furthermore, does not damage the surrounding great vessels, and the right atrial appendage does not need to be removed, which can reduce the death rate.

Figure 8:
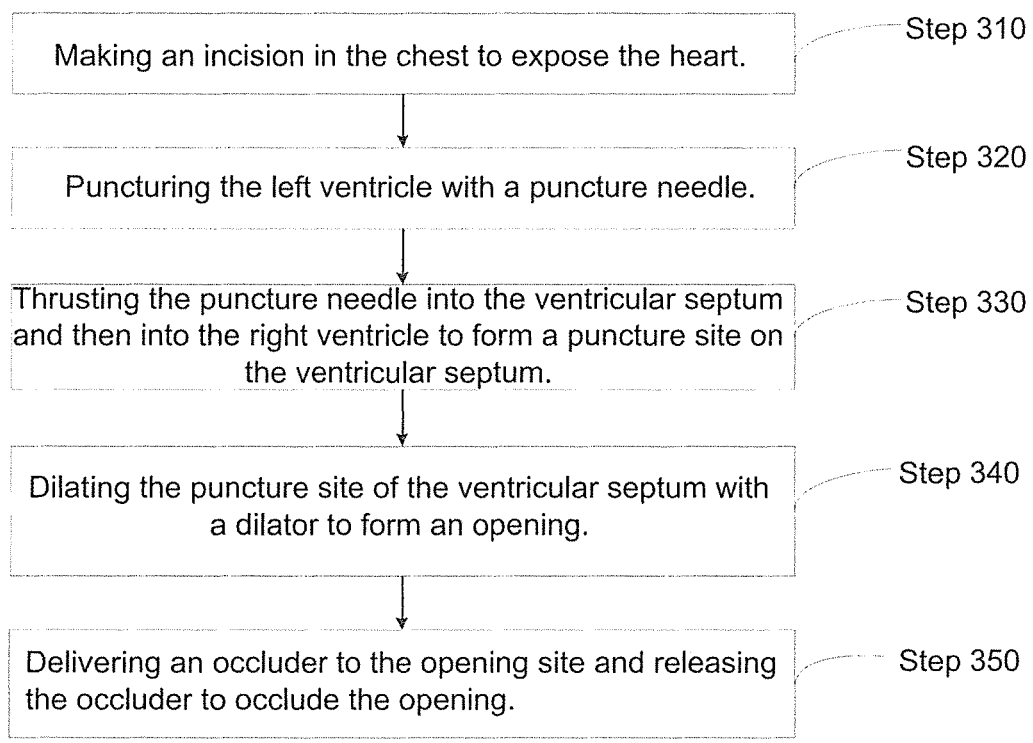
FIG. 8 is a flow chart of an implantation method according to yet another embodiment of the present disclosure.

Referring to FIG. 8, an implantation method of another embodiment includes the following steps:

Step 310: Making an incision in the chest to expose the heart.

Step 320: Puncturing the left ventricle with a puncture needle.

Step 330: Thrusting the puncture needle into the ventricular septum and then into the right ventricle to form a puncture site on the ventricular septum.

Steps 310, 320 and 330 are the same as Steps 110, 120 and 130 respectively, and will not be described in detail herein.

Step 340: Dilating the puncture site of the ventricular septum with a dilator to form an opening.

Step 340 is the same as Step 240 and is not described in detail herein.

Step 350: Delivering an occluder to the opening site and releasing the occluder to occlude the opening.

Figure 9:
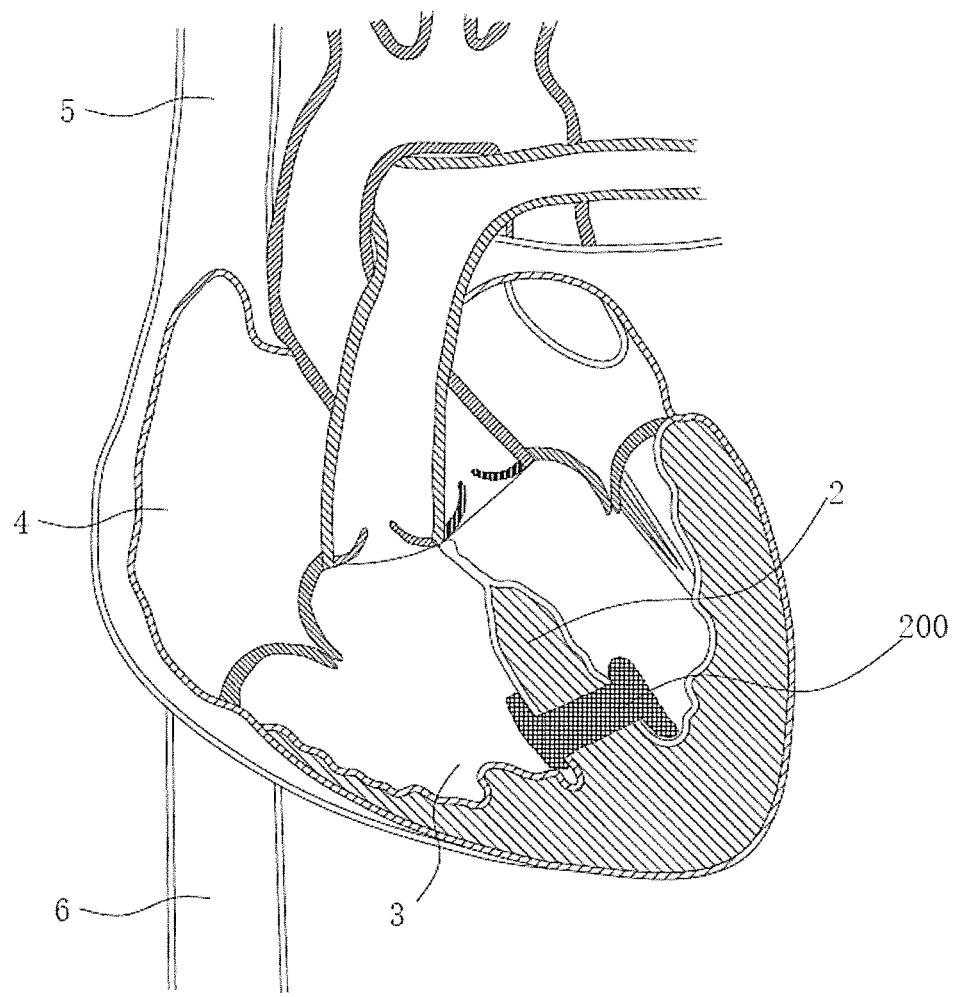
FIG. 9 is a schematic diagram of the state after an interventional device is implanted according to one embodiment of the present disclosure.

In one embodiment, when a right passageway is established by using the capturer 30 before the opening is formed, an interventional device 200 (e.g. an occluder) is sequentially introduced via the femoral vein, the inferior vena cava 6, the superior vena cava 5 and the right atrium 4 into the right ventricle 3 after the opening is formed, and is further released after reaching the ventricular septum 2 to occlude the opening in the ventricular septum 2, as shown in FIG. 9.

In another embodiment, when a right passageway is not established by using the capturer 30 before the opening is formed, the right passageway, (i.e. a passageway communicating the femoral vein, the inferior vena cava 6, the superior vena cava 5, the right atrium 4, the right ventricle 3 and the left ventricle 1) is first established by using the capturer 30 after the opening is formed. Then, an interventional device 200 is introduced along the right passageway, and is released after reaching the ventricular septum 2 to occlude the opening in the ventricular septum 2.

In another embodiment, when a right passageway is not established by using the capturer 30 before the opening is formed, an interventional device 200 is introduced from the left passageway. That is, the interventional device 200 is introduced along a path of left ventricle 1, and the ventricular septum 2, and then released. The shorter path for implanting the interventional device 200 of this embodiment facilitates shortening the operation time.

The implantation method of the present disclosure adopts an ostomy method that reduces the death rate, and improves the implantation success rate.

Furthermore, when both the left passageway and right passageway are established by using one guide wire 20 according to this method, the surgeon can select either the left passageway or the right passageway during implantation of the interventional device 200, so the present disclosure has a wide range of applicability.

The various technical features of the above-described embodiments may be in any combination. In order to simplify the description, all possible combinations of the various technical features in the above-described embodiments are not described. However, the combinations of these technical features should be considered to fall within the scope contained in this specification as long as they are not contradictive.

The embodiments described above represent only a few implementation modes of the present disclosure, which are described in more specificities and details, but are not to be construed as limiting the scope of the disclosure. It should be appreciated that for those of ordinary skill in the art that numerous variations and modifications may be made to the disclosure without departing from the spirit or scope of the present disclosure. Therefore, the protection scope of the disclosure is as set forth in the claims below.

The invention claimed is:

1. An ostomy method, comprising the following steps:
making an incision in the chest to expose the heart;
puncturing the left ventricle wall with a puncture needle;
thrusting the puncture needle into the ventricular septum and then into the right ventricle to form a puncture site on the ventricular septum; and
dilating the puncture site of the ventricular septum with a dilator to form an opening.

2. The ostomy method according to claim 1, wherein the step of puncturing the left ventricle wall with a puncture needle and the step of thrusting the puncture needle into the ventricular septum and then into the right ventricle to form a puncture site on the ventricular septum are carried out under ultrasound guidance, and the puncture needle is perpendicular or substantially perpendicular to the ventricular septum when the puncture needle is thrust into the ventricular septum.

3. The ostomy method according to claim 1, wherein before the step of dilating the puncture site of the ventricular septum with a dilator, threading a guide wire into the puncture needle, the ostomy further comprising the step of establishing a path communicating the femoral vein, the inferior vena cava, the superior vena cava, the right atrium, the right ventricle and the left ventricle after the guide wire is captured by a capturer.

4. The ostomy method according to claim 3, wherein the guide wire has two free ends located outside a living body, and wherein one free end is close to the femoral vein and the other free end is close to the left ventricle.

5. The ostomy method according to claim 4, wherein the step of dilating the puncture site of the ventricular septum with a dilator comprises introducing the dilator from the free end that is close to the left ventricle of the guide wire along the guide wire into the ventricular septum via the left ventricle to dilate the puncture site to form the opening.

6. The ostomy method according to claim 4, wherein the step of dilating the puncture site of the ventricular septum with a dilator comprises introducing the dilator from the free end that is close to the femoral vein of the guide wire along the guide wire into the ventricular septum via a path that communicates the femoral vein, the inferior vena cava, the superior vena cava, the right atrium, and the right ventricle to dilate the puncture site to form the opening.

7. The ostomy method according to claim 3, wherein the step of establishing a path communicating the femoral vein, the inferior vena cava, the superior vena cava, the right atrium, the right ventricle and the left ventricle after the guide wire is captured by a capturer comprises:

introducing the capturer from a path communicating the femoral vein, the inferior vena cava, the superior vena cava, the right atrium, and the right ventricle, or from a path communicating the femoral vein, the inferior vena cava, and the superior vena cava;

withdrawing the capturer along a path communicating the right ventricle, the right atrium, the superior vena cava, the inferior vena cava, the femoral vein, or along a path communicating the superior vena cava, the inferior vena cava, the femoral vein, and releasing the guide wire after the guide wire is captured by the capturer, thereby establishing the path communicating the femoral vein, the inferior vena cava, the superior vena cava, the right atrium, the right ventricle and the left ventricle.

8. The ostomy method according to claim 1, wherein the ostomy method is performed under electrocardiographic monitoring.

9. An ostomy method, comprising the following steps:
making an incision in the chest to expose the heart;
puncturing the left ventricle wall with a puncture needle;
thrusting the puncture needle into the ventricular septum and then into the right ventricle to form a puncture site on the ventricular septum;
threading a guide wire into the puncture needle to introduce the guide wire into a living body; and
introducing a dilator along the guide wire into the ventricular septum to dilate the puncture site to form an opening.

10. The ostomy method according to claim 9, wherein in the step of introducing a dilator along the guide wire into the ventricular septum to dilate the puncture site to form an opening, the dilator is introduced along the guide wire from the left ventricle into the ventricular septum.

11. The ostomy method according to claim 9, wherein before the step of introducing a dilator along the guide wire into the ventricular septum to dilate the puncture site to form an opening, the ostomy further comprises establishing a path communicating the femoral vein, the inferior vena cava, the superior vena cava, the right atrium, the right ventricle and the left ventricle after the guide wire is captured by a capturer; and in the step of introducing a dilator along the guide wire into the ventricular septum to dilate the puncture site to form an opening, the dilator is introduced along the guide wire into the ventricular septum from a path communicating the femoral vein, the inferior vena cava, the superior vena cava, the right atrium, and the right ventricle.

12. The ostomy method according to claim 9, wherein the step of puncturing the left ventricle with a puncture needle and the step of thrusting the puncture needle into the ventricular septum and then into the right ventricle to form a puncture site on the ventricular septum are carried out under ultrasound guidance, and the puncture needle is perpendicular or substantially perpendicular to the ventricular septum when the puncture needle is thrust into the ventricular septum.

13. An implantation method, comprising the following steps:
making an incision in the chest to expose the heart;
puncturing the left ventricle with a puncture needle;
thrusting the puncture needle into the ventricular septum and then into the right ventricle to form a puncture site on the ventricular septum;
dilating the puncture site of the ventricular septum with a dilator to form an opening; and
delivering an occluder to the opening site and releasing the occluder to occlude the opening.

14. The implantation method according to claim 13, wherein before the step of dilating the puncture site of the ventricular septum with a dilator, the method further includes the steps of threading a guide wire into the puncture needle, and establishing a path communicating the femoral vein, the inferior vena cava, the superior vena cava, the right atrium, the right ventricle and the left ventricle after the guide wire is captured by a capturer.

15. The implantation method according to claim 14, wherein the step of dilating the puncture site of the ventricular septum with a dilator to form an opening comprises introducing the dilator along the guide wire into the ventricular septum from a path communicating the femoral vein, the inferior vena cava, the superior vena cava, the right atrium, the right ventricle, and the ventricular septum to dilate the puncture site to form the opening.

16. The implantation method according to claim 15, wherein before the step of delivering an occluder to the opening site and releasing the occluder to occlude the opening, further comprising withdrawing the dilator out of a living body from the ventricular septum, the right ventricle, the right atrium, the superior vena cava, the inferior vena cava and the femoral vein.

17. The implantation method according to claim 14, wherein the step of dilating the puncture site of ventricular septum with a dilator to form an opening comprises introducing the dilator along the guide wire from the left ventricle into the ventricular septum to dilate the puncture site to form the opening.

18. The implantation method according to claim 14, wherein before the step of delivering an occluder to the opening site and releasing the occluder to occlude the opening, the implantation further comprises a step of withdrawing the dilator out of a living body from the left ventricle.

19. The implantation method according to claim 14, wherein in the step of delivering an occluder to the opening site and releasing the occluder to occlude the opening, the occluder is delivered along a delivery path that communicates the femoral vein, the inferior vena cava, the superior vena cava, the right atrium, the right ventricle, and the ventricular septum.

20. The implantation method according to claim 13, wherein the step of puncturing the left ventricle with a puncture needle and the step of thrusting the puncture needle into the ventricular septum and then into the right ventricle to form a puncture site on the ventricular septum are carried out under ultrasound guidance, and the puncture needle is perpendicular or substantially perpendicular to the ventricular septum when the puncture needle is thrust into the ventricular septum.

* * * * *